United States Patent

Inamoto et al.

[11] 4,036,892
[45] July 19, 1977

[54] 4-EXO-HYDROXY-ENDO-TRICYCLO[5.2.2.0²,⁶]UNDEC-8-ENE

[75] Inventors: Yoshiaki Inamoto; Yoshiaki Fujikura; Hiroshi Ikeda; Naotake Takaishi, all of Wakayama, Japan

[73] Assignee: Kao Soap Co., Ltd., Tokyo, Japan

[21] Appl. No.: 684,395

[22] Filed: May 7, 1976

[30] Foreign Application Priority Data

May 26, 1975 Japan .................. 50-62816

[51] Int. Cl.² .............................................. C07C 35/22
[52] U.S. Cl. .................. 260/617 F; 71/122; 252/522; 260/586 P; 260/586 G; 260/666 PY; 424/343
[58] Field of Search ........................... 260/617 F

[56] References Cited

U.S. PATENT DOCUMENTS

| | | | |
|---|---|---|---|
| 2,394,583 | 2/1946 | Bruson | 260/617 F |
| 2,404,787 | 7/1946 | Bruson | 260/617 F |
| 2,875,244 | 2/1959 | Bartlett et al. | 260/617 F |
| 3,345,419 | 10/1967 | Tinsley et al. | 260/617 F |

OTHER PUBLICATIONS

Traylor et al, "J.A.C.S.", vol. 85, pp. 2746–2752 (1963).
Traylor, "J.A.C.S.", vol. 86, pp. 244–248 (1964).
Brown et al, "J.A.C.S.", vol. 89, pp. 1524–1525 (1967).

Primary Examiner—Norman Morgenstern
Attorney, Agent, or Firm—Blanchard, Flynn, Thiel, Boutell & Tanis

[57] ABSTRACT

The compound 4-exo-hydroxy-endo-tricyclo[5.2.2.0²,⁶]-undec-8-ene having the formula (I):

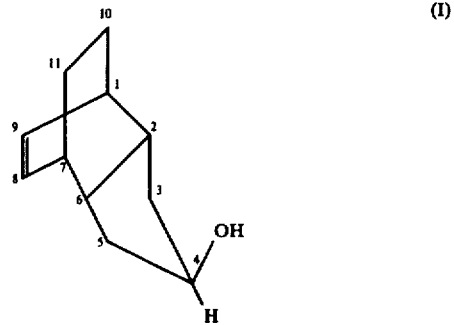

is prepared by subjecting endo-tricyclo[5.2.2.0²,⁶]undeca-3,8-diene having the formula (II):

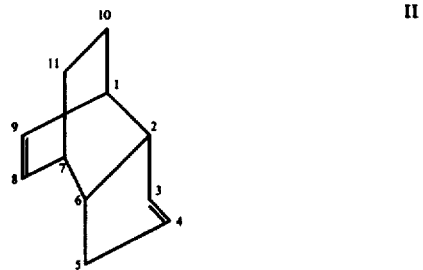

to oxymercuration and reduction with sodium borohydride.

1 Claim, No Drawings

4-EXO-HYDROXY-ENDO-TRICYCLO [5.2.2.0²,⁶]UNDEC-8-ENE

The present invention relates to the compound 4-exohydroxy-endo-tricyclo[5.2.2.0²,⁶]undec-8-ene, a novel tricyclic unsaturated alcohol having the formula (I):

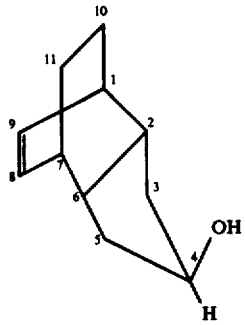

and a process for preparing same. More particularly, the invention relates to a process for preparing the formula (I) compound by subjecting endo-tricyclo[5.2.2.0²,⁶]undeca-3,8-diene having the formula (II):

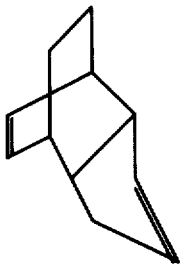

to oxymercuration and reduction with sodium borohydride.

The compound of formula (I) is a novel substance. Because it has a polycyclic aliphatic structure like those of natural sesquiterpene alcohols and synthetic tricyclic aliphatic alcohols such as adamantyl alcohol, this compound will have sustantially the same physiological activities as those known compounds, such as an antiviral activity, an antifungal activity and a plant-growth stimulating activity and it will also be useful as an active odor-imparting ingredient of perfume compositions. Still further, as a great number of natural and synthetic aliphatic polycyclic compounds are incorporated as modifying groups into various pharmaceutical compounds and physiologically active compounds to improve the effects of those compounds, the compound of the present invention can be utilized similarly to those known compounds.

Aliphatic polycyclic compounds, for example, adamantane derivatives are distinguished from linear aliphatic compounds and from aromatic compounds in the features that they can be used as bases and as additives of lubricating oil compositions, fiber oiling compositions and components thereof, rust preventing compositions, extreme pressure additives and synthetic macromolecular monomers. In view of the polycyclic structure of the compound of the present invention, the compound of the present invention will also have these valuable properties. Accordingly, the compound of the present invention is valuable, per se, and as an intermediate and it can be used in various fields.

According to the present invention, 4-exo-hydroxy-endo-tricyclo[5.2.2.0²,⁶]undec-8-ene having the formula (I) is synthesized by reacting endo-tricyclo[5.2.2.0²,⁶]undeca-3,8-diene having the formula (II) with mercuric acetate to effect a so-called oxymercuration and then reducing the resulting organic mercury intermediate with sodium borohydride.

It was found that the following three novel characteristics are involved in this reaction. More specifically, (1) even though two double bonds are present in the starting substance of formula (II), only the double bond at the 3-position participates in the reaction; (2) the substitution with the hydroxyl group is highly regiospecific and the substitution takes place substantially only at the 4-position; and (3) the steric arrangement of the hydroxyl group introduced into the 4-position is highly stereospecific and only the exo-isomer as shown in formula (I) is formed.

It is known that some olefins, especially monocyclic and cyclic olefins, are regiospecific and/or stereospecific in the oxymercuration reaction. However, the starting substance of formula (II) used in the present invention has not been investigated at all in this connection. Further, the diolefin of formula (II) has a structure quite different from the structures of compounds heretofore studied. Accordingly, the above specific properties of the starting substance of formula (II) could not have been predicted from the results of the research heretofore reported. Therefore, the above experimental facts can be said to be quite novel findings.

The fact that the unsaturated alcohol of formula (I) has the above-mentioned structure can be proved in the following manner.

The $^{13}C$ NMR spectrum of the compound (I) consists of 6 absorptions, and the relative intensity of one absorption is 1 and the relative intensity of each of the remaining 5 peaks is 2. From this fact, it is apparently proved that the hydroxyl group is substituted at the 4-position. In other words, if the hydroxyl group is substituted at any of the 3-, 8- and 9-positions, the molecule will be asymmetric all the $^{13}C$ NMR spectrum will have to show 11 absorptions. The $^{13}C$ signal having a relative intensity of 1 (attributed to the carbon atom at the 4-position) appears in a region of a lower magnetic field (73.6 ppm) than the other signals, and the influence of the substitution by the hydroxyl group is readily understood. Signals of olefinic carbon atoms at the 8- and 9-positions (relative intensity of 2) appear in a region of a much lower magnetic field (133.7 ppm). Thus, it is clearly indicated that the latter are olefinic carbon atoms.

From the fact that an unsaturated alcohol of the following formula (IV), which is different from the compound (I), is formed by oxidizing the compound (I) and then reducing the oxidized product with lithium aluminum hydride, it is apparent that the hydroxyl group at the 4-position is of the exo-arrangement. As is shown by the reaction formula given below, in the reduction of a polycyclic ketone with lithium aluminum hydride, it is established that the reagent approaches the exo-side of a reduced steric hindrance (the so-called steric approach control) and the resulting alcohol comes to have an endo-arrangement [see, for example G. R. Wenzinger and J. A. Ors, J. Org. Chem., 39, 2060 (1974), P. E. Schueler and Y. E. Rhodes, ibid, 39, 2063 (1974) and H.

C. Brown and W. J. Hammer, J. Amer. Chem. Soc., 89, 1524 (1967)].

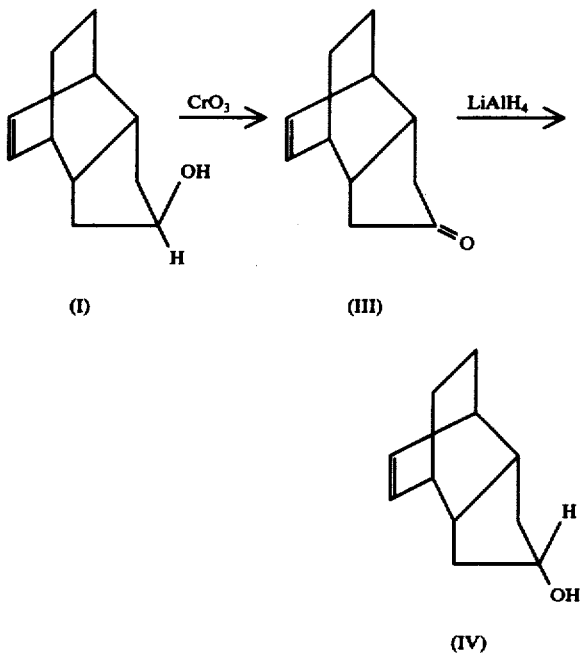

That is, the unsaturated alcohol (IV) necessarily takes the endo-arrangement as shown by formula (IV), and hence, the compound (I) having an arrangement different from that of the alcohol (IV) is an exo-alcohol of formula (I).

In practising the process of the present invention, the conventional method of oxymercuration and reduction with sodium borohydride [H. C. Brown et al, J. Org. Chem. 35, 1844 (1970)] can be directly applied to the starting substance (II). Since the selectivity of formulation of the formula (I) compound in this reaction is very high, as pointed out hereinabove, the formula (I) compound can be isolated from the reaction mixture very easily. That is, the formula (I) compound, of a high purity, can be obtained in a good yield by extracting the reaction mixture with a suitable organic solvent, for example, diethyl ether and recrystallizing the extract.

The diolefin (II) that is used as the starting substance in the process of the present invention can be prepared, for example, by Diels-Alder reaction between 1,3-cyclohexadiene and cyclopentadiene [Italian Patent No. 730 703 Dec. 1, 1966), Takaishi, Inamoto, Aigami, Tsuchihashi and Ikeda, Synth. Commun., 4, 225 (1974) and Takaishi, Inamoto and Aigami, J. Org. Chem., 40, 276 (1975)].

There will now be described a preparation of the starting substance (II), an Example of the preparation of the formula (I) compound and an Example showing the antiviral activity of the formula (I) compound.

Preparation

A 500 ml-capacity autoclave was charged with 30 g of 1,3-cyclohexadiene, 74.3 g of dicyclopentadiene and 50 mg of hydroquinone, and the inside atmosphere was replaced by nitrogen gas and the autoclave was sealed. The reaction was conducted at 200° C. for 8 hours. The reaction mixture was cooled and fractionated to obtain a fraction having a boiling point of 58° to 60° C. (under 3 mm Hg). Thus there was obtained 37 g (yield : 67%) of endo-tricyclo[5.2.2.0$^{2,6}$]undeca-3,8-diene.

Elementary Analysis Values: Found: C = 89.8%, H = 9.5%; Calculated for $C_{11}H_{14}$: C = 90.4%, H = 9.7%.

Infrared Absorption Spectrum (neat, cm$^{-1}$): 1650, 1620, 1615, 1370, 1350, 710, 680

Mass Spectrum, m/e (relative intensity): 146 (M$^+$, 11), 117 (3), 115 (3), 91 (5), 81 (7), 80 (100), 79 (28), 68 (12)

NMR (CDCl$_3$ solvent, TMS internal standard, δ): 6.15 (multiplet, 2H), 5.55 (multiplet, 2H), 3.0 - 1.0 (multiplet, 10H)

EXAMPLE 1

12.8 g (0.4 mole) of mercuric acetate was dissolved in 200 ml of water and 200 ml of tetrahydrofuran, and 58.4 g. (0.4 mole) of endo-tricyclo[5.2.2.0$^{2,6}$]undeca-3,8-diene (II) was added dropwise to the resulting yellow solution under agitation at room temperature. After the yellow color disappeared from the reaction mixture, the agitation was continued for 1 hour and the reaction mixture was cooled to −10° C. Then, 400 ml of a 3N aqueous solution of sodium hydroxide was added to the reaction mixture and 400 ml of a 3N aqueous solution of sodium hydroxide in which 7.56 g of sodium borohydride had been dissolved was further added. The mercury that precipitated by reduction was separated by filtration, and the aqueous layer was recovered and extracted with diethyl ether. The ether extract was combined with the organic layer and the mixture was dried on anhydrous magnesium sulfate.

The low-boiling-point solvent was distilled off under reduced pressure, and the residual crude alcohol was recrystallized from n-hexane to give 54.2 g (0.33 mole) of needle-like crystals of 4-exo-hydroxy-endo-tricyclo[5.2.2.0$^{2,6}$]undec-8-ene (I), melting at 98° to 99° C. The yield was 82%.

Elementary Analysis Values: Found: C = 80.15%, H = 9.93%; Calculated for $C_{11}H_{16}O$: C = 80.44%, H = 9.83%.

Infrared Absorption Spectrum (cm$^{-1}$): 3290 ($\nu_{O-H}$), 3050 ($\nu_{=C-H}$), 1608 ($\nu_{C=C}$), 1020 ($\nu_{C-O}$), 940, 720

Mass Spectrum, m/e (relative intensity): 164 (M$^+$, 50), 121 (18), 108 (17), 92 (13), 91 (19), 83 (31), 80 (100), 79 (43), 77 (13)

NMR (CDCl$_3$ solvent, TMS internal standard, δ): 6.12 (multiplet, 2H, —HC=CH—), 4.18 (multiplet, 1H, —CHOH), 2.02 (singlet, 1H, OH), 2.6 - 1.0 (multiplet, 12H)

$^{13}$C NMR (CDCl$_3$ solvent, TMS internal standard, ppm) (degree of multiplicity, intensity): 25.3 (triplet, 2), 34.4 (doublet, 2), 40.8 (triplet, 2), 42.5 (doublet, 2), 73.6 (doublet, 1), 133.7 (doublet, 2)

EXAMPLE 2

Chick embryo fibroblasts were cultured for 2 to 3 days in a test tube according to the monolayer culture method and were inoculated with Newcastle disease virus of about 128 HAU (hamagglutination units). A culture medium of the stepwise dilution system containing a compound as listed below was added to the upper layer and the culturing was continued for 48 hours at 37° C. The anti-viral effect was evaluated based on the hemagglutination reaction. The results obtained are shown below.

| Compound | Concentration (μg/ml) | % HAU* | CT** |
|---|---|---|---|
| 4-exo-hydroxy-endo-tricyclo[5.2.2.0^{2,6}]-undec-8-ene | 125 | 2.7 | + |
|  | 62 | 13 | ± |
|  | 16 | 70 | — |
|  | 8 | 85 | — |
| adamantylamine hydrochloride | 500 | below 1 | + |
|  | 250 | 9 | ± |
|  | 125 | 100 | — |

Notes:

*: % HAU = $\dfrac{\text{HAU in sample containing test compound (dilution times inhibiting hemagglutination)}}{\text{HAU in untreated sample}} \times 100$

**: CT indicates the degree of the damage to chick embryo cells by the test compounds damage ± : small eruptions were formed on the cell surface
+ : cells of the monolayer parted from the tube wall
++ : cells were rounded or destroyed Thus, the formula (I) compound exhibits a more intense anti-viral activity than that of adamantylamine hydrochloride, a known useful anti-viral substance. The formula (I) compound can be used in the same way as adamantylamine hydrochloride, adjusting the dosage amounts as needed to reflect the more intense anti-viral activity of the formula (I) compound.

The embodiments of the invention in which an exclusive property of privilege is claimed are defined as follows:

1. A compound having the formula

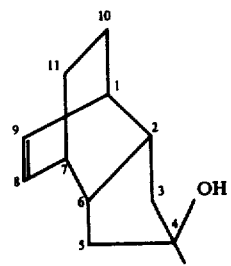

* * * * *